United States Patent
Zhu (10) Patent No.: US 11,583,829 B2
(45) Date of Patent: Feb. 21, 2023

(54) POLYMER FOR SEPARATION OF ANALYTES AND METHODS FOR PREPARATION AND USE OF SAME

(71) Applicant: Chroma Global Holdings Ltd., Vancouver (CA)

(72) Inventor: Fake Zhu, Beijing (CN)

(73) Assignee: Chroma Global Holdings Ltd., Vancouver (CA)

(*) Notice: Subject to any disclaimer, the term of this patent is extended or adjusted under 35 U.S.C. 154(b) by 277 days.

(21) Appl. No.: 17/013,296

(22) Filed: Sep. 4, 2020

(65) Prior Publication Data

US 2021/0069675 A1 Mar. 11, 2021

(30) Foreign Application Priority Data

Sep. 5, 2019 (CN) .......................... 201910836930.3

(51) Int. Cl.
*B01D 15/20* (2006.01)
*B01J 20/26* (2006.01)
*B01J 20/28* (2006.01)
*B01J 20/285* (2006.01)
*B01J 20/30* (2006.01)
*C08F 212/08* (2006.01)
*C08F 212/36* (2006.01)
(Continued)

(52) U.S. Cl.
CPC ........ *B01J 20/2808* (2013.01); *B01D 15/206* (2013.01); *B01J 20/261* (2013.01); *B01J 20/285* (2013.01); *B01J 20/3085* (2013.01); *C07D 311/80* (2013.01); *C08F 212/08* (2013.01); *C08F 212/36* (2013.01); *C08K 5/14* (2013.01); *C08K 5/315* (2013.01); *B01J 2220/52* (2013.01); *B01J 2220/54* (2013.01); *B01J 2220/58* (2013.01)

(58) Field of Classification Search
CPC ... B01D 15/206; B01J 20/261; B01J 20/2808; B01J 20/285; B01J 20/3085; B01J 2220/52; B01J 2220/54; B01J 2220/58; C07D 311/80; C08F 212/08; C08F 212/36; C08K 5/14; C08K 5/315
See application file for complete search history.

(56) References Cited

U.S. PATENT DOCUMENTS 4,444,961 A * 4/1984 Timm ...................... B01J 19/18
 521/38
9,375,657 B2 6/2016 Oroskar et al.
(Continued)

FOREIGN PATENT DOCUMENTS

| CN | 101954299 | 1/2011 | |
|----|-----------|--------|---|
| CN | 107607644 | 8/2019 | |
| EP | 0334641 A2 * | 9/1989 | ............... A23L 2/78 |

*Primary Examiner* — Benjamin L Lebron
(74) *Attorney, Agent, or Firm* — Greenberg Traurig, LLP (57) ABSTRACT

A polymer for liquid chromatography or solid phase extraction is provided. The polymer is prepared by polymerizing styrene and divinylbenzene to form a styrene-divinylbenzene copolymer; soaking the styrene-divinylbenzene copolymer in a swelling agent to form nano-scale micropores; and soaking the microporous styrene-divinylbenzene copolymer in methanol. When packed in a chromatographic column, the polymer can be used to produce produce natural health or medicinal products from *Cannabis* species, for example, industrial hemp.

20 Claims, 3 Drawing Sheets

(51) Int. Cl.
 *C08K 5/14* (2006.01)
 *C08K 5/315* (2006.01)
 *C07D 311/80* (2006.01)

(56) References Cited

U.S. PATENT DOCUMENTS

| | | | |
|---|---|---|---|
| 10,189,762 | B1 | 1/2019 | Oroskar et al. |
| 10,604,464 | B2 | 3/2020 | Oroskar et al. |
| 2015/0129501 | A1 | 5/2015 | Oroskar et al. |
| 2019/0010107 | A1 | 1/2019 | Oroskar et al. |
| 2019/0010110 | A1 | 1/2019 | Oroskar et al. |
| 2020/0047083 | A1 | 2/2020 | Antharavally et al. |
| 2020/0172503 | A1 | 6/2020 | Oroskar et al. |

* cited by examiner

POLYMER FOR SEPARATION OF ANALYTES AND METHODS FOR PREPARATION AND USE OF SAME

REFERENCE TO RELATED APPLICATIONS

This application claims the benefit of the priority of Chinese patent application No. 201910836930.3 which was filed on 5 Sep. 2019 and is hereby incorporated herein by reference for all purposes.

TECHNICAL FIELD

The technology described herein relates a polymer for separation of analytes and methods for preparation and use of same. More specifically, the technology described herein relates to a polymer that can be used as the stationary phase in liquid chromatography and/or solid phase extraction. The technology described herein also relates to a method of preparing the polymer and different uses of the polymer. Some embodiments relate to use of the polymer in separation applications to produce natural health or medicinal products from the *Cannabis* species, for example, industrial hemp.

BACKGROUND

Liquid chromatography and solid phase extraction are separation techniques. These techniques separate analytes by contacting an analyte-containing solution with a solid material. Liquid chromatography has been widely used in the pharmaceutical, food, and chemical industries. A liquid chromatography system has two phases: a stationary phase and a mobile phase. An analyte-containing solution is injected into the stationary phase and moved through the stationary phase by the mobile phase. As the mobile phase passes through the stationary phase, the mobile phase moves the analytes through the stationary phase at different speeds. The different speeds result from the fact that the analytes interact to varying degrees with the stationary phase. Analytes are separated based on their different physiochemical interactions with the mobile phase and the stationary phase. The different physiochemical interactions may be based on molecular size, charge, hydrophobicity, specific binding interactions and/or the like.

Solid phase extraction is an extraction technique, which typically relies on selective retention mechanisms. Similar to liquid chromatography, solid phase extraction also has two phases: a stationary phase and a mobile phase. Analytes are typically separated based on their partition coefficients and adsorption capacities. During a separation run, the composition of the mobile phase changes as the analytes partition between and interact with the two phases. An equilibrium condition is typically reached, such that the various analytes are retained by the stationary phase for different periods of time, thereby allowing the separation of the analytes as the mobile phase passes through the stationary phase.

Liquid chromatography and solid phase extraction share a number of similarities. For example, the same chromatographic principles apply to them in that separation occurs based on the differences in physical and/or chemical properties of the analytes.

Also, in both liquid chromatography and solid phase extraction, stationary phase selection is an important consideration to ensure the effective and precise separation of analytes. The stationary phase is often produced by suitable (e.g. chemical or physical) modification of particulate substrates. Such modified substrates may provide a high-surface structure to support the stationary phase. The physicochemical properties of substrates can directly affect the efficiency, selectivity and stability of the stationary phase. Some commonly used substrates include alumina, silica, titania/zirconia, and polymer substrates. The stationary phase substrates used in liquid chromatography can often be used in solid phase extraction.

There is a general desire for an improved polymer-based substrate for liquid chromatography and/or solid phase extraction. Such an improved polymer-based substrate may be useful to produce natural health or medicinal products from the *Cannabis* species, including, without limitation, industrial hemp. For example, such a polymer-based substrate may be used to obtain, isolate, and/or purify *cannabis* extracts or hemp extracts.

Public interest in the production of natural health and medicinal products from the *Cannabis* species has been growing. *Cannabis* (*Cannabis sativa* L.) is an herbaceous plant, which is believed to have originated in India, Iran, the Northwestern Himalayas, and China. The history of *cannabis* goes back thousands of years and has been used for medicinal, therapeutic, and spiritual purposes. *Cannabis* has long been considered to have medicinal properties, ranging from treatment of cramps, migraines, pain, and nausea. Despite the very long history of medicinal *cannabis* use, *cannabis* consumption and cultivation have been criminalized in many parts of the world. For example, *cannabis* is a "Schedule I substance" in the U.S.'s Controlled Substances Act meaning that *cannabis* is characterized as a highly dangerous substance with potential for addiction. Recently, there appears to be a trend towards *cannabis* legalization for both medicinal and recreational uses. For example, Canada legalized *cannabis* for recreational use in 2018.

Although *cannabis* has long been used as a hypnotic sedative for the treatment of hysteria, paranoia, epilepsy, neuropathic insomnia, migraine, pain, and dysmenorrhea, there is a desire for further research into the medicinal and therapeutic properties of *cannabis*. *Cannabis* contains a wide range of chemical compounds, including terpenes, phenols, fatty acids, amino acids, sugars and cannabinoids. More than 100 cannabinoids have been identified and some notable ones are (—)-trans-$\Delta$-9tetrahydrocannabinol (THC), cannabidiol (CBD), cannabinol (CBN), cannabigerol(CBG), and cannabichromene(CBC). THC and CBD may be the most well-known cannabinoids. There is a desire to obtain high purity cannabinoids for many purposes, such as, by way of non-limiting example, to facilitate the development of pharmacological investigations. There is a general desire for an improved method for isolating and purifying cannabinoids.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Aspects of the present invention include methods for making a polymer that can be used for liquid chromatography and/or solid phase extraction and different applications for the polymer.

One aspect of the invention provides a method for making a polymer that can be used for liquid chromatography and/or solid phase extraction. The method comprises: polymerizing styrene and divinylbenzene to form a styrene-divinylbenzene copolymer; soaking the styrene-divinylbenzene copolymer in a swelling agent to form nano-scale micropores; and soaking the microporous styrene-divinylbenzene copolymer in methanol.

The step of polymerizing styrene and divinylbenzene may comprise: adding the styrene, the divinylbenzene, a polymerization initiator, and a pore-forming agent to an organic medium to form a mixture; and heating the mixture to initiate a polymerization reaction and to form, by the polymerization reaction, the styrene-divinylbenzene copolymer.

The molar ratio of the styrene to the divinylbenzene may be in a range of 0.8:1 to 1.2:1.

The polymerization initiator may comprise one or more of azobisisobutyronitrile and benzoyl peroxide.

The number of moles of the polymerization initiator used may be 1 to 2% of the styrene.

The pore-forming agent may comprise polyethylene glycol.

The organic medium may comprise a mixture of polyethylene glycol and liquid paraffin. The volume ratio of polyethylene glycol and liquid paraffin is in a range of 0.8:1 to 1.2:1.

The swelling agent may comprise one or more of chloroform, methanol or ethanol.

The number of moles of the swelling agent used may be 30 to 40% of the styrene.

The styrene-divinylbenzene copolymer may be soaked in the swelling agent at a temperature between 30° C. and 40° C. The styrene-divinylbenzene copolymer may be soaked in the swelling agent for 3 to 4 hours.

The nano-scale micropores may have a pore diameter of 0.4 to 0.6 nm.

The step of soaking the microporous styrene-divinylbenzene copolymer in methanol may modify the surfaces of the nano-scale micropores to allow diffusion of an analyte into and out of the pores to achieve separation and recovery of the analyte when the polymer is used in liquid chromatography or solid phase extraction. The surfaces of the nano-scale micropores may be smoothed.

The microporous styrene-divinylbenzene copolymer may have a particle size of 100 to 200 mesh and a pore diameter of 0.4 to 0.6 nm.

In relation to the different applications pf the polymer, the polymer can be used to produce natural health or medicinal products from *Cannabis* species, for example, industrial hemp. In particular, the polymer can be used to isolate and purify cannabinoids from a *cannabis* sample; the polymer can be used to remove pesticide active ingredients from a *cannabis* sample.

One embodiment relates to a method for preparing a *cannabis* extract. The method comprise: preparing a chromatographic column packed with the polymer of the present invention; obtaining *cannabis* plant material; extracting the *cannabis* plant material with a solvent to thereby produce a *cannabis* extract; passing the *cannabis* extract through the chromatographic column arranged to fractionate at least one cannabinoid out from the *cannabis* extract; and collecting the fraction containing the cannabinoid.

The *cannabis* plant material may comprise industrial hemp.

The cannabinoid contained in the fractions may comprise THC, CBD, CBN, CBG, CBC, CBDV, THCBD, THCBG, THCBC, THCBDV, and other naturally occurring cannabinoids in the *cannabis* plant material.

The *cannabis* plant material may be first dried and/or ground before the extraction step.

The (extraction) solvent may be an organic solvent, for example any one of methanol, ethanol, ethylene glycol, acetone, ethyl acetate, pentane, n-hexane, heptane, and petroleum ether. Other suitable solvents known in the art or combinations thereof may be used.

The collected fraction(s) may be concentrated, for example by evaporating the mobile phase solvent.

The collected fraction(s) may undergo a crystallization step so that pure CBD can be obtained.

If the *cannabis* plant material is industrial hemp and if the industrial hemp sample contains pesticide residues, the pesticide residues may be removed by passing the *cannabis* extract through the chromatographic column arranged to fractionate pesticide active ingredients out from the *cannabis* extract; and collecting the fraction containing the pesticide active ingredients.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Various chemical substances are described herein. Such chemical substances may not be absolute pure. Instead, such substances may have a purity of at least about 50%, at least about 60%, at least about 70%, at least about 80%, at least about 90%, at least about 95%, at least about 97%, at least about 98%, or at least about 99% pure. The expression "substantially pure" means a purity of greater than 95%. For example, "substantially pure" cannabinoid preparation means that the preparation having a chromatographic purity of greater than 95%, 96%, 97%, 98% or 99%.

As used in this specification, the terms "about" or "approximately" mean a value within +/−10% of the stated value unless specified otherwise, and either one of these terms connotes that strict compliance with the numeric value recited is not critical but some variation is permissible and still within the scope of the various embodiments described herein.

As used herein, "cannabis" includes all plants belonging to the genus Cannabis, which includes both hemp and marijuana, and includes all Cannabis species such as Cannabis indica, Cannabis sativa, Cannabis ruderalis, and other such Cannabis species as may be identified or reclassified from time to time, and further includes industrial hemp, and the like.

As used herein, "industrial hemp" refers to cannabis plants that have a low content of THC, i.e. less than 0.5% THC on the dry plant mass.

As used herein, "chaff" refers to the remaining cannabis plant material after the seeds are removed by a threshing process.

Embodiments of the present invention provide a polymer for separation of analytes and methods for preparation and use of same. Aspects of the present invention include methods for making a polymer that can be used for liquid chromatography and/or solid phase extraction and different applications of the polymer. With respect to the different applications, the polymer can be used to produce natural health or medicinal products from Cannabis species, for example, industrial hemp. In particular, the polymer can be used, among other applications, to isolate and purify cannabinoids from a cannabis sample; and to remove pesticide active ingredients from a cannabis sample.

A Polymer and Method for Preparation of Same

Figure 1:
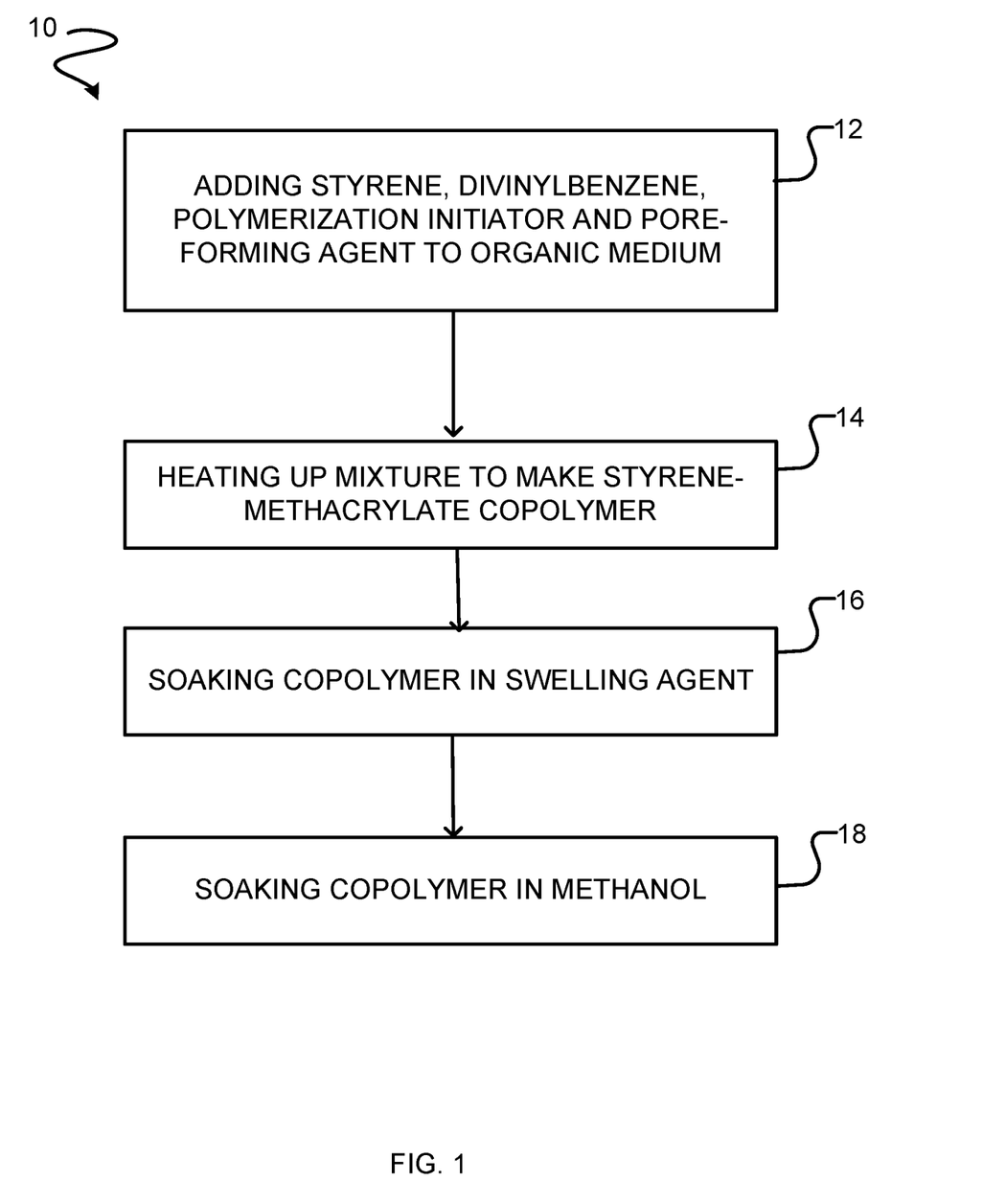
FIG. 1 is a block diagram showing a method for making a polymer for liquid chromatography and/or solid phase extraction according to a particular example embodiment.

FIG. 1 schematically illustrates a method 10 for preparing a polymer which may be used for separating analytes (e.g. for liquid chromatography and/or solid phase extraction) according to a particular example embodiment.

Method 10 starts in step 12 which involves adding styrene, divinylbenzene, a polymerization initiator and a pore-forming agent to an organic medium.

In some embodiments, the molar ratio of the styrene to the divinylbenzene is 1:1. In some embodiments, this molar ratio can be in a range of 0.8:1 to 1.2:1 or about 0.8:1 to 1.2:1.

In some embodiments, the polymerization initiator comprises one or more of azobisisobutyronitrile and benzoyl peroxide. In some embodiments, the polymerization initiator is one or more of azobisisobutyronitrile and benzoyl peroxide. In some embodiments, the number of moles of polymerization initiator used in step 12 may be 1% to 2% of the styrene. In some embodiments, the number of moles of polymerization initiator may be in a range of 0.5-5% (or about 0.5-5%) of the styrene.

In some embodiments, the pore-forming agent comprises polyethylene glycol. In some embodiments, the pore-forming agent is polyethylene glycol.

In some embodiments, the organic medium comprises a mixture of polyethylene glycol and liquid paraffin. In some embodiments, the organic medium is a mixture of polyethylene glycol and liquid paraffin. The volume ratio of polyethylene glycol and liquid paraffin may be 1:1. In some embodiments, this volume ratio can be in a range of 0.8:1 to 1.2:1 (or about 0.8:1 to 1.2:1).

At step 14, the mixture from step 12 is heated to initiate a polymerization reaction and to thereby form a styrene-divinylbenzene copolymer. In some embodiments, the mixture is heated to a temperature in a range between 50° C. and 90° C. The temperature in step 14 may be any one or more of 55±2.5° C., 60±2.5° C., 65±2.5° C., 70±2.5° C., 75±2.5° C., 80±2.5° C. and 85±2.5° C., for example. The temperature selected in step 14 may be maintained for 2 to 3 hours or for some other suitable time to facilitate the polymerization reaction.

During the step 14 heating process, the mixture is optionally mixed/stirred to help facilitate the polymerization reaction. In some non-limiting example embodiments, the mixture is mixed during the step 14 heating process at a stirring speed of 100 to 150 rpm (or about 100 to 150 rpm).

The styrene-divinylbenzene copolymer may have a particle size in a range of 100 to 200 mesh.

Method 10 then proceeds to step 16, where the styrene-divinylbenzene copolymer is washed and soaked in a swelling agent to create nano-scale micropores. Such nano-scale micropores may have a pore diameter of 0.4 nm (4 Å) to 0.6 nm (6 Å) (or about 0.4 nm-0.6 nm). Step 16 may comprise rinsing the nano-scale micropores with water and methanol until the styrene-divinylbenzene copolymer is anhydrous. The styrene-divinylbenzene copolymer is then soaked in the swelling agent. In some embodiments, the swelling agent comprises one or more of chloroform, methanol, and ethanol. In other embodiments, the swelling agent is one or more of chloroform, methanol, and ethanol. The number of moles of swelling agent used may be in a range of 30 to 40% of the styrene. In some embodiments, the number of moles of swelling agent used may be 20 to 50% (or about 20 to 50%) of the styrene. The pore diameter varies depending on the amount of swelling agent used and the time duration that the styrene-divinylbenzene copolymer is soaked in the swelling agent.

In some embodiments, step 16 is carried out at a temperature in a range between 30° C. and 40° C. This step 16 temperature may be any one or more of 30±2° C., 32±2° C., 34±2° C., 36±2° C., 38±2° C. and 40±2. ° C., for example. The temperature may be maintained for 3 to 4 hours or for some other suitable time to facilitate the creation of nano-scale micropores.

The output of step 16 is a microporous styrene-divinylbenzen copolymer.

Method 10 then proceeds to step 18, which involves soaking the microporous styrene-divinylbenzene copolymer in methanol or ethanol. This step 18 soaking procedure modifies the surfaces of the microporous styrene-divinylbenzene copolymer to allow diffusion of analytes into and out of the pores to achieve the desired separation and analyte recovery. For example, the step 18 soaking procedure may smoothen the surface of the micropores and wash out debris from the micropores.

After step 18, the microporous styrene-divinylbenzene copolymer may have a particle size in a range of 100 to 200 mesh and a pore diameter of 0.4 nm (4 Å) to 0.6 nm (6 Å) (or about 0.4 nm to 0.6 nm).

Another aspect of the present invention provides a polymer for liquid chromatography and solid phase extraction, wherein the polymer is made in accordance with method 10. The polymer may comprise or be a microporous styrene-divinylbenzene copolymer having a particle size of 100 to 200 mesh and a pore diameter of 0.4 nm (4 Å) to 0.6 nm (6 Å) (or about 0.4 nm to 0.6 nm).

Another aspect of the present invention provides a separation column for liquid chromatography, wherein the separation column is packed with a polymer made in accordance with method 10.

Another aspect of the present invention provides a solid phase extraction cartridge, wherein the cartridge is packed with a polymer made in accordance with method 10.

Another aspect of the present invention provides a method for preparing a substrate for solid phase extraction, the method comprising (1) adding styrene, divinylbenzene, an initiator, and a pore-forming agent to a liquid medium for polymerization to form polymeric beads;

(2) adding a swelling agent to the polymeric beads to carry out a reaction to form nano-scale micropores; and (3) soaking the microporous polymeric beads with methanol.

In step (1), the mixture may be stirred at a speed in a range of 100 to 150 RPM. The polymeric beads in step (1) may have a particle size of 100 to 200 mesh.

The reaction temperature of step (1) may be in 50 to 90° C. The procedures of step (1) may be performed for a period of 2 to 3 hours.

The liquid medium may comprise or be a mixture of polyethylene glycol and liquid paraffin.

The initiator may comprise or be one or more of: azobisisobutyronitrile and benzoyl peroxide.

The pore-forming agent may comprise or be polyethylene glycol.

The molar ratio of the styrene to the divinylbenzene used in step (1) may be 1:1±20%.

The amount of the initiator used in step (1) may be 1 to 2% (or about 1 to 2%) by mole of the styrene.

In step (2), the swelling agent may comprise or be any one of methanol, ethanol, and chloroform. The amount of the swelling agent used may be 30 to 40% (or about 30 to 40%) by mole of the styrene.

In step (2), the reaction temperature may be 30 to 40° C. The procedures of step (2) may be performed for a period in a range of 3 to 4 hours.

Use of the Polymer in Isolation and Purification Techniques

The polymer made in accordance with method 10 can be used in separation applications to produce natural health or medicinal products from *Cannabis* species, for example, industrial hemp. For example, the polymer made in accordance with method 10 may be packed in a solid phase chromatographic column/cartridge and the column/cartridge can then be used to isolate and purify cannabinoids using solid phase extraction. In another embodiment, the polymer made in accordance with method 10 may be packed in a liquid chromatography column and the column can then be used to isolate and purify cannabinoids using liquid chromatography separation.

The polymer made in accordance with method 10 can be packed in an industrial-scale chromatography column and then used to isolate and purify cannabinoids from a large volume of *cannabis* plant material. At least Examples 4-8 (discussed below) show that when the polymer made in accordance with method 10 is packed in an industrial-scale chromatography column, the polymer retains its physical structure and can be used in separation applications to produce substantially pure cannabinoids from a large volume of *cannabis* plant material. In some circumstances, the polymer's usability in industrial-scale chromatography is advantageous. For example, it may be difficult to procure marijuana because its cultivation is highly regulated. On the other hand, it may be relatively easy to procure industrial hemp as there is little legislative restriction on its cultivation. The polymer's usability in industrial-scale chromatography allows it to process a large volume of industrial hemp to extract and purify the 0.3% THC that hemp contains on the dry plant mass.

Figure 2:
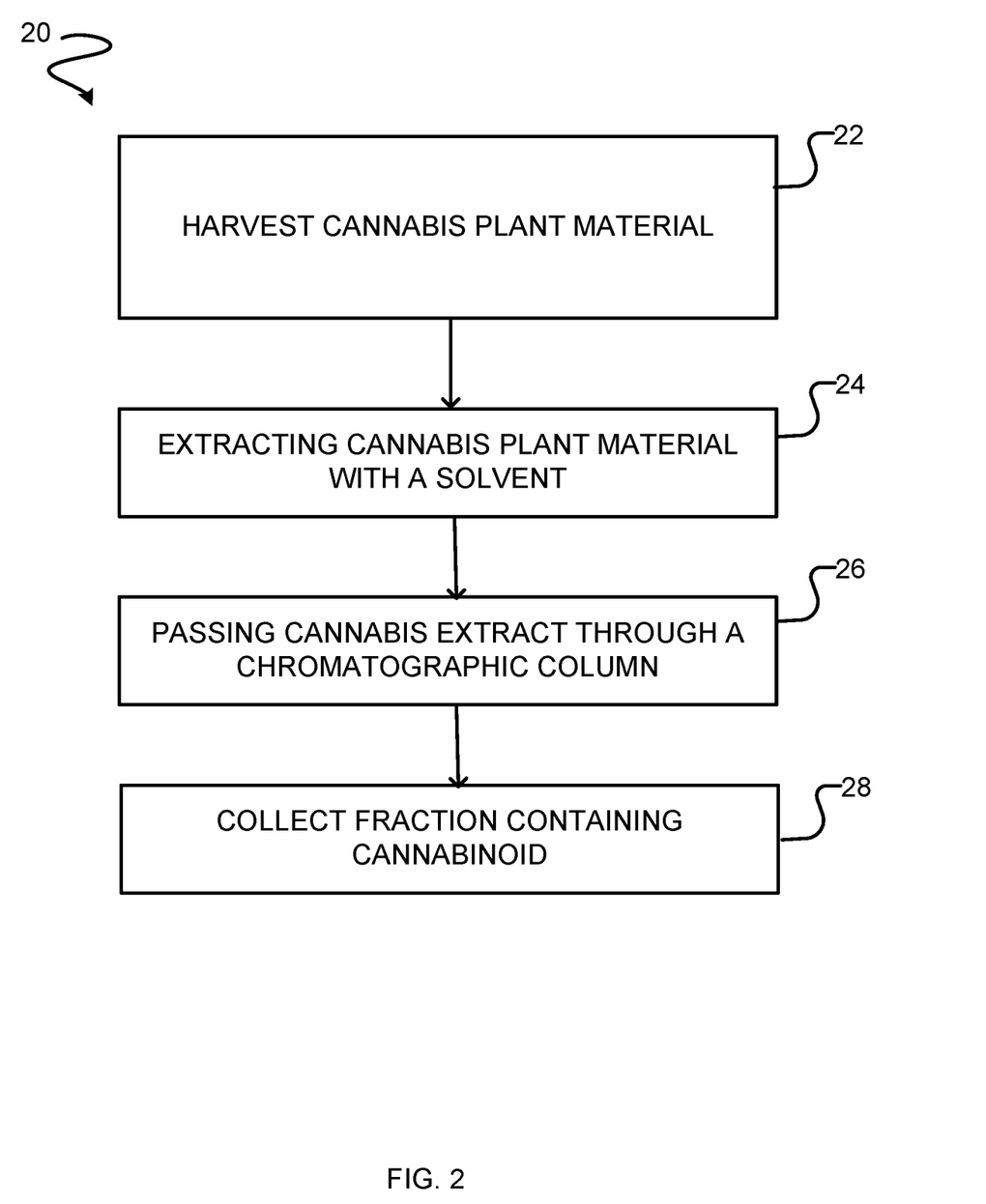
FIG. 2 is a block diagram showing a method for isolating and purifying cannabinoids according to a particular example embodiment.

FIG. 2 schematically illustrates a method 20 for preparing a *cannabis* extract. Method 20 uses a chromatographic column packed with polymer (made in accordance with method 10) to isolate and purify cannabinoids. Some interesting cannabinoids comprise, without limitation, THC, CBD, CBN, CBG, and CBC. Method 20 may be used to prepare high-purity cannabinoids. In some embodiments, method 20 enables the preparation and production of a single-cannabinoid product that has a purity of higher than 90%, 95%, 98%, or 99%. Method 20 may also be implemented in an industrial scale.

In general, method 20 comprises:
- step 22—harvesting *cannabis* plant material;
- step 24—treating the harvested *cannabis* plant material with a solvent to produce an extract;
- step 26—passing the extract through a chromatographic column arranged to fractionate a cannabinoid out from the extract, wherein the chromatographic column is packed with the polymer made in accordance with method 10; and
- step 28—collecting the fraction containing the cannabinoid.

At step 22, *cannabis* plant material is harvested. *Cannabis* plant material may include, for example, the cola, bract, trichromes, sugar leaves, fan leaves, pistil, stem, and stalk of a *Cannabis sativa* L. plant. *Cannabis* plant material may include the leaves, flower, and stem of an industrial hemp plant. In some embodiments, *Cannabis* plant material does not include the seeds but includes only the chaff (e.g. to the extent possible).

The harvested *cannabis* plant material may dried and then finely divided, ground or pulverized before the extraction step 24. For example, the harvested *cannabis* plant material may be first dried up, perhaps at room temperature or some other temperature that is less than 80° C., until the moisture content is less than 8%, 5%, or 3%. The dried material may be then be pulverized and sieved to a size of less than 0.1 mm. In other embodiment, the harvested *cannabis* plant material may be extracted green, i.e. without being dried first.

At step 24, the harvested *cannabis* plant material is treated with a solvent to produce an extract. The harvested *cannabis* plant material is soaked in a solvent to extract cannabinoids. The solvent may be an organic solvent, for example any one of methanol, ethanol, ethylene glycol, acetone, ethyl acetate, pentane, n-hexane, heptane, and petroleum ether. Other suitable solvents known in the art or combinations thereof may be used.

The time of residency of the harvested *cannabis* plant material in the solvent may be up to about 2-4 hours although the time of residency may vary based on the cannabinoids to be extracted, whether the harvested *cannabis* plant is first dried, and how finely the harvested *cannabis* is pulverized.

The mixing ratio of the harvested *cannabis* plant material to the solvent is such that the harvested *cannabis* plant material can be suspended in the solvent during the extraction process. For example, the amount of the solvent used may be about 6-8 L/kg of the weight of the harvested *cannabis* plant material.

Once the solvent treatment process is complete, any insoluble material is removed (perhaps by filtration) and the resulting *cannabis* extract may be further processed before it is purified per step 26. For example, the resulting *cannabis* extract may be diluted before it is purified. Alternatively, the resulting *cannabis* extract may be concentrated by evaporation of the solvent and then mixed with a second solvent before the extract is purified.

In some other embodiments, the *cannabis* extract (obtained in step 24) is prepared by one or more other known extraction method(s), for example $CO_2$ extraction.

At step 26, the *cannabis* extract obtained in step 24 (or otherwise) is passed through a chromatographic column arranged to fractionate a cannabinoid out from the extract, wherein the chromatographic column is packed with the polymer made in accordance with method 10. The chromatographic column may be a stainless steel column with a height to diameter ratio of 8:1 and a volume of 400 L. The chromatographic column may have a stainless steel column with a height to diameter ratio of 5:1 and a volume of 500 L. At least Examples 4-8 (discussed below) show that when the polymer made in accordance with method 10 is packed in these industrial-scale chromatography columns, the polymer is able to retain its physical structure and can be used in separation applications to produce substantially pure cannabinoids from a large volume of *cannabis* plant material. A person skilled in the art would appreciate that the column may be of any suitable dimensions and may be made of any suitable materials.

The chromatographic column packed with the polymer made in accordance with method 10 is configured to fractionate cannabinoids out of the eluent. As the *cannabis* extract is passed through the chromatographic column, cannabinoids are differentially retained in the chromatographic column. The retained cannabinoids then pass through the chromatographic column by a mobile phase. The mobile phase may run in an isocratic elution mode or a linear gradient mode. Depending on which cannabinoids are targeted, the mobile phase composition may differ. The mobile phase composition may also differ depending on the solvent used in the solvent extraction step. For example, if the target cannabinoid is THC, the mobile phase may be a mixture of water and at least one of methanol, ethanol, acetone, ethyl acetate, and acetonitrile, or a mixture of heptane and ethyl acetate. In a particular embodiment, *cannabis* extract is prepared by an ethanol extraction process and the resulting *cannabis*-ethanol extract is diluted into a 30% aqueous solution (with 30% of the volume being water). The aqueous solution is filtered to remove any insoluble matter and the supernatant is injected/pumped into the chromatographic column. The cannabinoid compounds contained in the *cannabis*-ethanol extract are moved through the column by a mobile phase, which may be 80% ethanol. In another example, *cannabis* extract may be prepared by a heptane extraction process. To isolate and purify THC from the heptane-*cannabis* extract, a mixture of ethyl acetate and heptane may be used as the mobile phase. If the target cannabinoid is CBD, the mobile phase may be a mixture of water and at least one of methanol, ethanol, acetone, ethyl acetate and acetonitrile. Water may take up about 10-30% of the final volume.

At step 28, fraction containing the cannabinoid of interest is collected. The fraction may be concentrated by evaporating the mobile phase. The removal of the mobile phase may be carried out in a single-effect concentration tank, a multi-effect concentration tank, or a membrane machine. The removal of the mobile phase may be carried out in a combination of the membrane machine and the single-effect concentrator.

In some embodiments, a further crystallization step is performed. For example, once the mobile phase is removed, the resulting product may be a mixture of cannabinoids. For example, to isolate and obtain a high-purity CBD, CBD may be crystalized and isolated from the other cannabinoids present in the mixture. For example, the crystallization step may be carried out in ethanol, methanol, n-hexane or heptane, wherein the mixture of cannabinoids is first dissolved/mixed with one of ethanol, methanol, n-hexane or heptane. The crystallization step may be carried out at a temperature of about −5° C. and for duration between 4 hours and 8 hours.

The crystallization step may be followed by a drying step. The crystalline product of CBD may be dried in a vacuum drying oven, a double cone vacuum dryer, or a microwave dryer. In some embodiments, the drying temperature is between 50° C. and 60° C. and the drying time is between 4 hours and 6 hours. The dried crystalline product of CBD may have a purity of greater than 90%, 95%, or 99%.

Several different cannabinoids may be purified from a single extract.

Use of the Polymer in Removal of Pesticide Residues

Pesticide active ingredients in *cannabis* products are often strictly regulated. For example, Health Canada has set limits of quantification for pesticide active ingredients in fresh *cannabis, cannabis* plants, and dried *cannabis*. Some example pesticides used against pests that can be found on *cannabis* include: abamectin, acephate, acequinocyl, acetamiprid, aldicarb, benzovindiflupyr, bifenazate, bifenthrin, carbaryl, carbofuran, chlorantraniliprole, cyfluthrin, daminozide, dimethoate, endosulfan sulfate, ethoprophos, etoxazole, fenoxycarb, iprodione, kinoprene, malathion, metalaxyle, myclobutanil, naled, novaluron, oxamyl, paclobutrazol, permethrin, phosmet, resmethrin, tebuconazole, and thrifloxystrobin.

Pesticides may be similarly used during the cultivation of industrial hemp. Some example pesticides include α-naphthaleneacetic acid, clethodim, octanoyl bromoxynil, chlorpyrifos, and cyhalothrin. If industrial hemp is used to produce substantially pure cannabinoids, it would be desirable to remove any pesticide active ingredients.

The polymer made in accordance with method 10 can be used to remove pesticide active ingredients from a *cannabis* extract. For example, the polymer made in accordance with method 10 may be packed in a solid phase chromatographic column and the column can then be used to remove pesticide active ingredients from a *cannabis* product using solid phase extraction. In another embodiment, the polymer made in accordance with method 10 may be packed in a liquid chromatography column and the column can then be used to remove pesticide active ingredients from a *cannabis* product using liquid chromatography separation.

Figure 3:
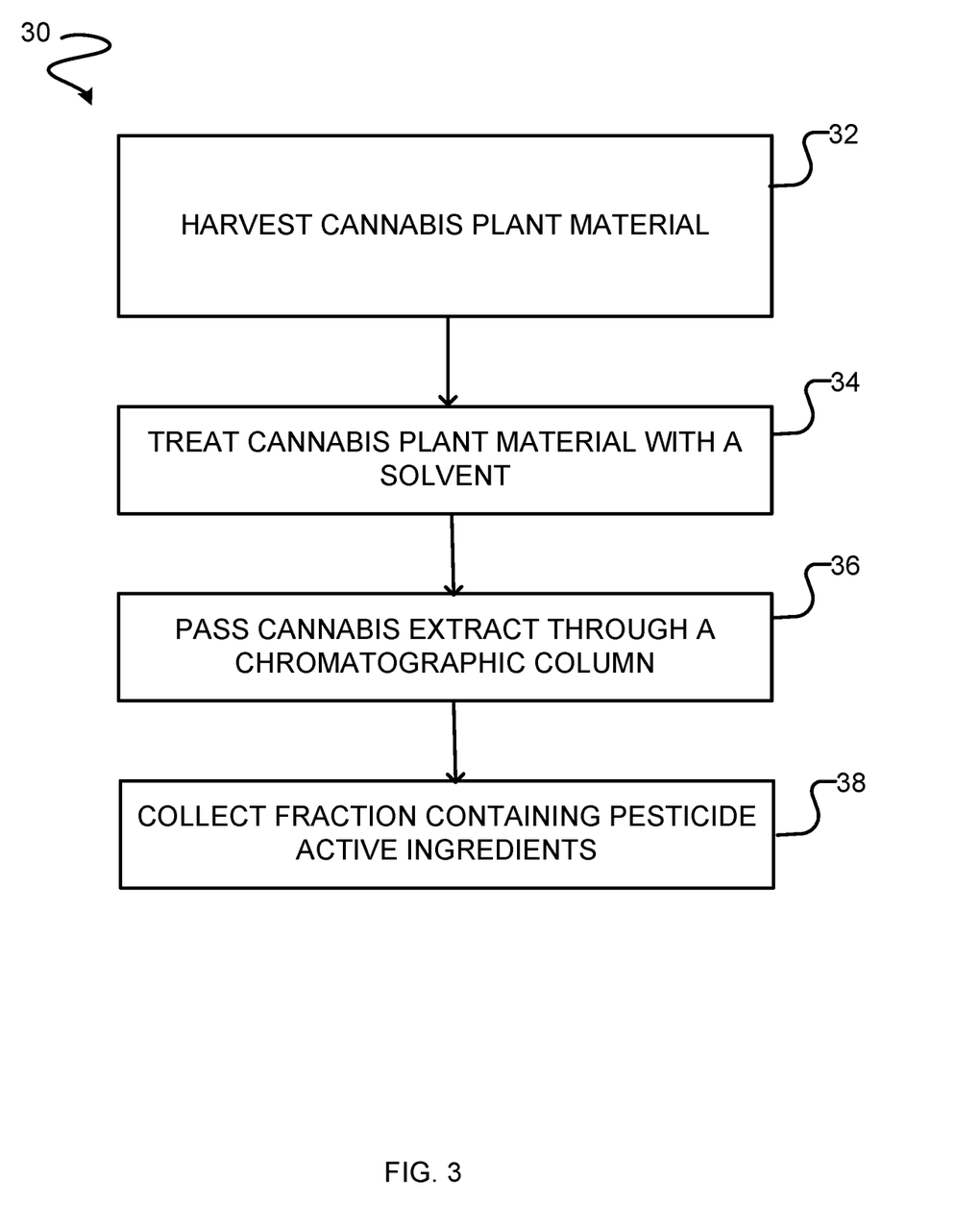
FIG. 3 is a block diagram showing a method for removing pesticide active ingredients from a *cannabis* product according to a particular example embodiment.

FIG. 3 schematically illustrates a method 30 for using a chromatographic column packed with polymer (made in accordance with method 10) to remove pesticide active ingredients from a *cannabis* extract. Method 30 is similar to method 20 in principle.

Additionally, method 30 and method 20 may be combined to produce substantially pure cannabinoids that are free from pesticide active ingredients. Steps of method 30 that correspond to the steps of method 20 are shown in numerals incremented by 10. These similar steps between method 20 and method 30 may not be described in detail to avoid unnecessarily obscuring the description. In general, method 30 comprises:

step 32—harvesting *cannabis* plant material;

step 34—treating the harvested *cannabis* plant material with a solvent to produce an extract;

step 36—passing the extract through a chromatographic column arranged to fractionate pesticide active ingredients out from the extract, wherein the chromatographic column is packed with the polymer made in accordance with method 10; and step 38—collecting the fraction containing the pesticide active ingredients.

At step 36, a *cannabis* extract containing pesticide active ingredients and cannabinoids is injected into and passed through the chromatographic column. As the *cannabis* extract is passed through the chromatographic column, cannabinoids are differentially retained in the chromatographic column. The polymer made in accordance with method 10 enables the pesticide active ingredients to pass through the chromatographic column by the mobile phase before the cannabinoids. Without being bound by theory, the inventor believes that the pesticide active ingredients pass through the column faster than the cannabinoids because of (i) the physical structure of the polymer and/or (ii) the different physical property between the pesticide active ingredients and cannabinoids, e.g. water solubility.

At step 38, the fraction containing the pesticide active ingredients is collected. The removed pesticide active ingredients may be denatured and then disposed of.

Example 1—Polymer Preparation 400 ml of polyethylene glycol and 100 ml of liquid paraffin were added to a 1000 ml four-necked flask.

The mixture was heated and stirred at 50° C. for 30 minutes.

40 g of divinylbenzene, 25 g of styrene and 0.8 g of azobisisobutyronitrile were added to the mixture. The mixture was stirred and heated. The mixture was then incubated at 80° C. for 3 hours.

0.2 g of benzoyl peroxide was added to the mixture. The mixture was heated and stirred at 90° C. for 3 hours. The stirring speed was at 150 rpm.

The mixture was then poured out and filtered to obtain polymeric beads having a particle size of 150 to 200 mesh.

The polymeric beads were washed with hot water 3 times and then with methanol until the polymeric beads became anhydrous.

The polymeric beads were loaded in a glass column of 40 mm in diameter and 400 mm in height.

The polymeric beads were soaked in chloroform (30% by mole of styrene) for 3 hours. The temperature was kept at 30° C.

Chloroform was released. The polymeric beads were washed with petroleum ether until no wax.

Petroleum ether was released. The polymeric beads were washed with methanol until clear.

Methanol was released.

The polymeric beads were poured out to obtain the prepared solid phase chromatography packing with a particle size of 150-200 mesh and a pore diameter of 0.1-0.15 nm.

Example 2—Polymer Preparation 400 ml of polyethylene glycol and 50 ml of liquid paraffin were added to a 1000 ml four-necked flask. The mixture was heated and stirred at 50° C. for 30 minutes.

40 g of divinylbenzene, 25 g of styrene and 1 g of azobisisobutyronitrile were added to the mixture. The mixture was then heated and stirred at 90° C. for 3 hours. The stirring speed was 150 rpm.

The mixture was poured out and filtered to obtain polymeric beads having a particle size of 150 to 200 mesh.

The polymeric beads were washed with hot water 3 times and then with the methanol until the polymeric beads became anhydrous.

The polymeric beads were placed in a glass column of 40 mm in diameter and 400 mm in height.

The polymeric beads were soaked in chloroform for 3 hours (40% by mole of styrene). The temperature was kept at 30° C.

The chloroform was released, and the polymeric beads were washed with petroleum ether until no wax.

Petroleum ether was released and the polymeric beads were washed with methanol until clear.

The methanol was released and the polymeric beads were poured out to obtain a solid phase chromatography polymer with a degree of 150-200 mesh and a pore diameter of 0.1-0.15 nm.

Example 3—THC Isolation and Purification

The solid phase chromatography polymer prepared by Example 1 and Example 2 was used to separate THC in *cannabis* plant material by liquid chromatography. The obtained THC extract had of about 98%.

In general, the THC extract was obtained by:
(1) treating *cannabis* plant material with a solvent to obtain an extract, and then performing liquid chromatography separation; collecting the fourth to seventh column volume of the effluent, that is, a solution containing tetrahydrocannabinol; and
(2) the effluent was sequentially removed by a solvent to obtain high-purity tetrahydrocannabinol.

The *cannabis* plant material included the flower stalk of hemp. The *cannabis* plant material was dried so that the moisture content was less than 8%. The dried *cannabis* plant material was then ground to have a particle size of less than 0.1 mm.

The solvent used in step (1) may be any one of methanol, ethanol, ethylene glycol, acetone, ethyl acetate, pentane, n-hexane, heptane and petroleum ether. The solvent may be used in an amount of 6-8 L/kg of the *cannabis* plant material.

In step (1), the conditions for the liquid chromatography separation were as follows:
the column was a stainless steel column with a height to diameter ratio of 8:1 and a volume of 400 L;
the mobile phase may be a mixture of at least two of water, methanol, ethanol, acetone, ethyl acetate and acetonitrile or a mixture of heptane and ethyl acetate;
isocratic elution;
the flow rate was 2 to 3 times the column volume per hour.

The purity of the isolated THC extract was 95%. The purity of tetrahydrocannabinol was determined as follows:
Agilent High Pressure Liquid Chromatograph, Model 1220;
Column: EXTEND-C-18 4.6*250 mm 5 um;
Mobile phase: acetonitrile:aqueous phosphoric acid=70:30;
Detection wavelength: 220 nm;
Flow rate: 1.1 ml/min;
Column temperature: 35° C.

In particular, 200 kg of the chaff of industrial hemp was dried and pulverized to less than 0.1 mm by a pulverizer. The resulting *cannabis* sample had a water content of less than 8%.

The *cannabis* sample was loaded into a solvent extraction equipment and was extracted by 90% ethanol. For each gram of *cannabis* sample, 8 ml of 90% ethanol was used to extract the cannabinoids contained in the *cannabis* sample.

Once the solvent extract process was complete, the *cannabis* extract was diluted with water so that the water took up about 30% in volume of the diluted extract. The diluted extract was filtered to remove any insoluble by filtration.

The supernatant was pumped into a column that was a stainless steel column with a height to diameter ratio of 8:1 and a volume of 400 L. The stainless steel column was packed with the polymer made in Example 1.

The supernatant passed through the column. The column temperature was kept at room temperature.

The supernatant was eluted by 80% ethanol (the mobile phase). The flow rate was about 800 L/hr and 1200 L/hr.

Several fractions of the column volume were collected. All fractions were analyzed at a detection wavelength of 220 nm to determine the presence of THC. The first 3 column fractions did not contain THC. The $4^{th}$ to $7^{th}$ column fractions contained THC.

The $4^{th}$ to $7^{th}$ column fractions were combined and ethanol was removed from the THC by a membrane machine and a single-effect concentrator.

The recovered THC had a purity of 95%.

About 80% of the THC present in the chaff was extracted.

Example 4—THC Isolation and Purification

Substantially pure THC may be obtained by chromatography and in particular, by:
(1) extracting *cannabis* by solvent, obtaining an extract, and then performing liquid chromatography; collecting the fourth to seventh column volume of the effluent, which is a solution containing THC; and
(2) removing the solvent to obtain high purity tetrahydrocannabinol THC.

The *cannabis* plant material may be the flower, leaves and stalk of industrial hemp. The *cannabis* plant material was dried to have a water content of less than 8% and ground to have a particle size of less than 0.1 mm.

In step (1), the solvent may be any one of methanol, ethanol, ethylene glycol, acetone, ethyl acetate, pentane, n-hexane, heptane and petroleum ether, preferably ethanol, pentane or heptane.

The solvent was used in an amount of 6 to 8 times of the weight of the *cannabis* plant material.

The conditions for liquid chromatography in step (1) were:
the polymer was the polymer made in Example 1 or Example 2;
the column was a stainless steel column with a 8:1 aspect ratio and a volume of 400 L;
the mobile phase was a mixture of at least two of: water, methanol, ethanol, acetone, ethyl acetate and acetonitrile; or a mixture of heptane and ethyl acetate;
isocratic elution;
column temperature was room temperature (e.g. 15~25° C.); and
the flow rate was 2 to 3 times the column volume per hour.

In step (2), the solvent removal was carried out in at least one of a single-effect concentration tank, a multi-effect concentration tank, and a membrane machine. An oil of high purity THC is obtained after solvent removal.

The purity of the THC was determined as follows:
Agilent High Pressure Liquid Chromatograph, Model 1220;
Column: EXTEND-C-18 4.6*250 mm 5 um;
Mobile phase: acetonitrile:aqueous phosphoric acid=70:30;
Detection wavelength: 220 nm
Flow rate: 1.1 ml/min
Column temperature: 35° C.

In particular, 200 kg of the chaff of industrial hemp was dried and pulverized to less than 0.1 mm by a pulverizer. The resulting *cannabis* sample had a water content of less than 8%.

The pulverized *cannabis* sample was loaded into a solvent extraction apparatus, and extracted with 1,600 L 90% ethanol. The resulting ethanol-*cannabis* extract contained THC and other cannabinoids.

The ethanol-*cannabis* extract was diluted with water so that 30% of the final volume was water. The diluted extract was filtered to remove any insoluble matter, and the supernatant was pumped into the chromatographic column packed with the polymer made in Example 1.

Cannabinoids were eluted using an isocratic mode of 80% ethanol. The flow rate was about 800 L/hr to 1200 L/hr and the column was kept at room temperature.

Fractions flowing out the chromatographic column were collected, wherein the volume each fraction was the same of the column volume, i.e. 400 L.

Fractions were analyzed for the presence of THC. The first three fractions did not contain THC and the $4^{th}$ to the $7^{th}$ fractions contained THC.

The $4^{th}$ to the $7^{th}$ fractions were combined and ethanol was removed using a membrane machine and a single effect concentrator.

The resulting THC product had a purity of 95%. About 80% of the THC present in the chaff was extracted.

Example 5—THC Isolation and Purification 200 kg of the chaff of industrial hemp was dried and pulverized to less than 0.1 mm by a pulverizer. The resulting *cannabis* sample had a water content of less than 8%.

The pulverized *cannabis* sample was loaded into a solvent extraction apparatus, and extracted with 1,600 L heptane. The resulting heptane-*cannabis* extract contained THC and other cannabinoids.

The heptane-*cannabis* extract was filtered to remove any insoluble matter, and the supernatant was pumped into the chromatographic column packed with the polymer made in Example 1.

Cannabinoids were eluted using an isocratic mode of a mixture of ethyl acetate and heptane having a volume ratio of 1:10. The flow rate was about 800 L/hr to 1200 L/hr and the column was kept at room temperature.

Fractions flowing out from the chromatographic column were collected, wherein the volume each fraction was the same of the column volume, i.e. 400 L.

Fractions were analyzed for the presence of THC. The first three fractions did not contain THC and the $4^{th}$ to the $7^{th}$ fractions contained THC.

The $4^{th}$ to the $7^{th}$ fractions were combined. Ethyl acetate and heptane were removed using a membrane machine and a single effect concentrator.

The resulting THC product had a purity of 95%. About 80% of the THC present in the chaff was extracted.

Example 6—CBD Isolation and Purification

Substantially pure CBD may be obtained by chromatography and in particular, by:
(1) treating industrial hemp by a solvent, obtaining an extract, and then performing liquid chromatography; collecting the third to fourth column volume of the effluent, which is a solution containing CBD; and
(2) removing the solvent and crystalizing CBD.

The flower, leaves and stalk of industrial hemp may be used as raw material. The hemp material was dried so that the water content was less than 5% and was ground to a particle size of less than 0.1 mm.

In step (1), the solvent may be any one of methanol, ethanol, ethylene glycol, acetone, ethyl acetate, pentane, n-hexane, heptane and petroleum ether. The solvent was used in an amount of 6 to 8 times of the weight of the hemp sample.

The conditions for the liquid chromatography separation were as follows:
the polymer was polymer made either in Example 1 or Example 2;
the chromatographic column was a stainless steel column with a 5:1 aspect ratio and a volume of 500 L;
the mobile phase was a mixture of at least one of methanol, ethanol, acetone, ethyl acetate and acetonitrile and water, wherein the ratio of water is 10-30%;
isocratic elution; and
the flow rate was 2 to 3 times the column volume per hour.

The fractions obtained may contain cannabinol (CBG), secondary cannabinol (CBV), cannabinol (CBN), and tetrahydrocannabinol (THC).

In step (2), the solvent (mobile phase) removal was carried out in at least one of a single-effect concentration tank, a multi-effect concentration tank, and a membrane machine. An oil of high purity CBD and other cannabinoids was obtained after solvent removal.

To obtain pure CBD, a crystallization step was carried out in ethanol, methanol, n-hexane or heptane, preferably in ethanol or heptane. The conditions of the crystallization step were:
the crystallization temperature was −2~−5° C.; and
the time was for 4 to 8 hours.

after the crystallization, a drying step was carried out in a vacuum drying oven, a double cone vacuum dryer or a microwave dryer. The drying conditions are as follows:
the drying temperature was about 50~60° C.; and
the time was for 4-6 hours.

Upon drying, a crystalline product of CBD having a purity greater than 99% was obtained.

The purity of the CBD was determined as follows:
Agilent High Pressure Liquid Chromatograph, Model 1220;
Column: EXTEND-C-18 4.6*250 mm 5 um;
Mobile phase: acetonitrile:aqueous phosphoric acid=70:30;
Detection wavelength: 220 nm;
Flow rate: 1.1 ml/min; and
Column temperature: 35° C.

In particular, 400 kg of the chaff of industrial hemp was dried and pulverized to less than 0.1 mm by a pulverizer. The resulting *cannabis* sample had a water content of less than 3%.

The pulverized *cannabis* sample was loaded into a solvent extraction apparatus, and extracted with 10,000 L methanol. The resulting methanol-*cannabis* extract contained CBD and other cannabinoids.

The methanol-*cannabis* extract was diluted with water so that 30% of the final volume was water. The diluted extract was filtered to remove any insoluble matter, and the supernatant was pumped into a stainless steel chromatographic column having a 5:1 aspect ratio and a volume of 500 L. The chromatographic column was packed with the polymer made in Example 1.

Cannabinoids were eluted using an isocratic mode of 80% methanol solution. The flow rate was 1000 L/hr to 1500 L/hr and the column was kept at room temperature.

Fractions flowing out from the chromatographic column were collected, wherein the volume each fraction was the same of the column volume, i.e. 500 L.

Fractions were analyzed for the presence of CBD at a detection wavelength of 220 nm. The first fraction did not contain CBD and the $2^{nd}$ and $3^{rd}$ fractions contained CBD. The $4^{th}$ to the $6^{th}$ fractions contained a mixture of CBG, CBV, and CBN.

The $2^{nd}$ to the $6^{th}$ fractions were combined and methanol was removed using a membrane machine and a single effect concentrator. The removed methanol was recycled and reused. A concentrated solution was obtained by removing 90% or more of methanol. The concentrated solution contained CBD, CBG, CBV, and CBN.

To isolate and purify CBD, the concentrated solution was mixed with a heptane solvent. The temperature of the mixture was lowered to about −5° C. so that CBD could be crystalized. The crystallization temperature was −5° C. and the crystallization time was 5 hours.

Once the crystallization step was complete, the CBD crystal was filtered and dried in a double cone vacuum dryer, where the drying temperature was 60° C. and duration was for 6 hours. During the drying process, the solvent was removed obtain a CBD product with a purity of 99% or higher.

Example 7—CBD Isolation and Purification 1000 kg of the chaff of industrial hemp was dried and pulverized to less than 0.1 mm by a pulverizer. The resulting *cannabis* sample had a water content of less than 5%.

The pulverized *cannabis* sample were loaded into a solvent extraction apparatus, and extracted with 25,000 L ethanol. The resulting ethanol-*cannabis* extract contained CBD and other cannabinoids.

The ethanol-*cannabis* extract was diluted with water so that 40% of the final volume was water. The diluted extract was filtered to remove any insoluble matter, and the supernatant was pumped into a stainless steel chromatographic column having a 5:1 aspect ratio and a volume of 500 L. The chromatographic column was packed with the polymer made in Example 1.

Cannabinoids were eluted using an isocratic mode of 70% ethanol solution. The flow rate was 1000 L/hr to 1500 L/hr and the column was kept at room temperature.

Fractions flowing out from Agilent High Pressure Liquid Chromatograph, Model 1220 were collected, wherein the volume each fraction was the same of the column volume.

Fractions were analyzed for the presence of CBD at a detection wavelength of 220 nm. The first fraction did not contain CBD and the $2^{nd}$ and $3^{rd}$ fractions contained CBD. The $4^{th}$ to the $6^{th}$ fractions contained a mixture of CBG, CBV, and CBN.

The $2^{nd}$ to the $6^{th}$ fractions were combined and ethanol was removed using a membrane machine and a single effect concentrator. The removed methanol was recycled and reused. A concentrated solution was obtained by removing 90% or more of ethanol. The concentrated solution contained CBD, CBG, CBV, and CBN.

To isolate and purify CBD, the concentrated solution was mixed with a heptane solvent. The temperature of the mixture was lowered to about −5° C. so that CBD could be crystalized. The crystallization temperature was −5° C. and the crystallization time was 5 hours.

Once the crystallization step was complete, the CBD crystal was filtered and dried in a double cone vacuum dryer, where the drying temperature was 60° C. and duration was for 6 hours. During the drying process, heptane was removed obtain a CBD product with a purity of 99% or higher.

Example 8—CBD Isolation and Purification 600 kg of the chaff of industrial hemp was dried and pulverized to less than 0.1 mm by a pulverizer. The resulting *cannabis* sample had a water content of less than 5%.

The pulverized *cannabis* sample were loaded into a solvent extraction apparatus, and extracted with 15,000 L heptane. The resulting heptane-*cannabis* extract contained CBD and other cannabinoids.

The heptane was removed to create a concentrated extract by evaporation.

The concentrated extract was mixed with a 60% ethanol solution at 60° C. The temperature was then lowered to room temperature. Any insoluble material was removed by filtration and the supernatant was pumped into a stainless steel chromatographic column a 5:1 aspect ratio and a volume of 500 L. The chromatographic column was packed with the polymer made in Example 1.

Cannabinoids were eluted using an isocratic mode of 70% ethanol solution. The flow rate was 1000 L/hr to 1500 L/hr and the column was kept at room temperature.

Fractions flowing out from Agilent High Pressure Liquid Chromatograph, Model 1220 were collected, wherein the volume each fraction was the same of the column volume.

Fractions were analyzed for the presence of CBD at a detection wavelength of 220 nm. The first fraction did not contain CBD and the $2^{nd}$ and $3^{rd}$ fractions contained CBD. The $4^{th}$ to the $6^{th}$ fractions contained a mixture of CBG, CBV, and CBN.

The $2^{nd}$ to the $6^{th}$ fractions were combined and ethanol was removed using a membrane machine and a single effect concentrator. The removed methanol was recycled and reused. A concentrated solution was obtained by removing 90% or more of ethanol.

The concentrated solution contained CBD, CBG, CBV, and CBN.

To isolate and purify CBD, the concentrated solution was mixed with a heptane solvent. The temperature of the mixture was lowered to about −5° C. so that CBD could be crystalized. The crystallization temperature was −5° C. and the crystallization time was 5 hours.

Once the crystallization step was complete, the CBD crystal was filtered and dried in a double cone vacuum dryer, where the drying temperature was 60° C. and duration was for 6 hours. During the drying process, heptane was removed obtain a CBD product with a purity of 99% or higher.

Example 9—Pesticide Active Ingredient Removal

Pesticide residues in industrial hemp may be removed by chromatography and in particular, by:
(1) treatment of hemp with a solvent to obtain an extract, followed by liquid chromatography, and fractional collection according to the following a)-c):
 a. collecting the first to second column volume of the effluent as a solution containing impurities and residual pesticides;
 b. collecting the third to fourth column volume of the effluent as a solution containing cannabidiol (CBD);
 c. collecting the fifth to sixth column volume of the effluent as a solution containing a mixture of cannabinol (CBG), cannabinol (CBV) and cannabinol (CBN);
(2) the solution described in (a) is removed by solvent to obtain a concentrated liquid containing residual pesticide, thereby realizing the removal of pesticide residues in the hemp extract.

The flower, leaf, and stem of industrial hemp may be used as raw material. The raw material was dried so that the water content was less than 5% and was ground to a particle size of less than 0.1 mm.

In step (1), the solvent was one of methanol, ethanol, acetone, acetonitrile, ethyl acetate, pentane, n-hexane, heptane and petroleum ether. The ratio of solvent to raw material was about 6-8:1.

In step (1), the liquid chromatography was carried out under the following conditions:
 the polymer was the polymer made in Example 1 or Example 2;
 the chromatographic column was a stainless steel column with a height to diameter ratio of 5:1 and a volume of 500 L;
 the separation temperature was 15-25° C.;
 the mobile phase was a mixture of at least one of methanol, ethanol, acetone, ethyl acetate, acetonitrile and water, wherein the water content was 10-30%;
 isocratic elution; and
 the flow rate was 2 to 3 times the column volume per hour.

In step (2), the solvent removal was carried out in a single-effect concentration tank, a multi-effect concentration tank, or a membrane machine.

In step (2)(a), pesticide residue may be denatured by:
 converting the concentrated pesticide-containing concentrate and hydrogen peroxide into $CO_2$ and water, thereby achieving harmless treatment of residual pesticides; and
 the reaction temperature was 80 to 100° C. and the time was 2 to 3 hours.

In step (2)(b), the post-treatment may have a solvent removal step and a crystallization step. The concentrate after removal of the solvent may be crystallized in ethanol, methanol, n-hexane or heptane, preferably in ethanol or heptane.

In step (2)(c), solvent may be removed to obtain substantially pure cannabinoids.

The purity of CBD, CNG, CBN, and CBV extracts was determined by:
 Agilent high pressure liquid chromatography, model 1220;
 Column: EXTEND-C-18 4.6*250 mm 5 um;
 Mobile phase: acetonitrile:aqueous phosphoric acid=70:30;
 Detection wavelength: 220 nm;
 Flow rate: 1.1 ml/min;
 Column temperature: 35° C.

The content of pesticide residues was determined as follows:
 Instrument: Agilent Gas Chromatograph 6890N
 Column: 30 m×0.32 mm capillary column Bonded DB-5 (5% benzyl silicone), film thickness 0.25 um,
 Temperature: oven temperature: 240° C.;
 Inlet temperature (gasification chamber) 260° C.;
 Detection chamber 280° C.;
 Gas flow rate: carrier gas (nitrogen) 2.0 ml/min;
 Air 300 ml/min;
 Hydrogen 30 ml/min;

Split ratio: 20:1
Injection volume: 1.0 μl 400 kg of the chaff of industrial hemp was dried and pulverized to less than 0.1 mm by a pulverizer. The resulting *cannabis* sample had a water content of less than 3%.

Pesticide active ingredients were added to the pulverized *cannabis* sample so that the final concentration was about 50-100 ppm.

The pulverized *cannabis* sample was loaded into a solvent extraction apparatus, and extracted with 10,000 L methanol.

The methanol-*cannabis* extract was diluted with water so that 30% of the final volume was water. The diluted extract was filtered to remove any insoluble matter, and the supernatant was pumped into a stainless steel chromatographic column with a height to diameter ratio of 5:1 and a volume of 500 L. The chromatographic column was packed with the polymer made in Example 1.

The mobile phase used was 70% methanol solution in an isocratic mode. The flow rate was about 1000 L/hr to about 1500 L/hr and the column was kept at room temperature (between 15° C. and 25° C.).

Fractions flowing out from the chromatographic column were collected, wherein the volume each fraction was the same of the column volume, i.e. 500 L.

Fractions were analyzed for the presence of cannabinoids and pesticide active ingredients at a detection wavelength of 220 nm. The first two fractions contained pesticide active ingredients. The $3^{rd}$ and $4^{th}$ fractions contained CBD. The $5^{th}$ to the $6^{th}$ fractions contained a mixture of CBG, CBV, and CBN.

The $3^{rd}$ and $4^{th}$ fractions were combined and methanol was removed using a membrane machine and a single effect concentrator. The removed methanol was recycled and reused. A concentrated solution was obtained by removing 90% or more of methanol. The concentrated solution contained CBD.

The $5^{th}$ to the $6^{th}$ fractions were combined and methanol was removed using a membrane machine and a single effect concentrator. The removed methanol was recycled and reused. A concentrated solution was obtained by removing 90% or more of methanol. The concentrated solution contained CBG, CBV, and CBN.

To isolate and purify CBD, the concentrated solution was mixed with a heptane solvent. The temperature of the mixture was lowered to about −5° C. so that CBD could be crystalized. The crystallization temperature was −5° C. and the crystallization time was 5 hours.

Once the crystallization step was complete, the CBD crystal was filtered and dried in a double cone vacuum dryer, where the drying temperature was 60° C. and duration was for 6 hours. During the drying process, the solvent was removed obtain a CBD product with a purity of 99% or higher.

The $1^{st}$ and $2^{nd}$ fractions were combined and methanol was removed using a membrane machine and a single effect concentrator. A concentrated solution was obtained by removing 90% or more of methanol. The concentrated solution contained the removed pesticide active ingredients. This concentrated solution was mixed with hydrogen peroxide. For each kg of the concentrated solution, 0.05 kg of hydrogen peroxide was added. The mixture was then heated to 80° C. for 2 hours to denature the removed pesticide active ingredients.

Example 10—Pesticide Active Ingredient Removal

A *cannabis* sample, namely flowers, leaves, and stem of an industrial hemp plant, was obtained.

The quantity of pesticide active ingredients in the *cannabis* sample was determined using Agilent Gas Chromatograph 6890N. The used parameters were: (i) column: 30 m×0.32 mm capillary column Bonded DB-5 (5% benzyl silicone), film thickness 0.25 um; (ii) temperature: oven temperature: 240° C.; (iii) inlet temperature (gasification chamber) 260° C.; (iv) detection chamber 280° C.; (v) gas flow rate: carrier gas (nitrogen) 2.0 ml/min; (vi) air 300 ml/min; (vii) hydrogen 30 ml/min; (x) Split ratio: 20:1; and (xi) injection volume: 1.0 μl. The content of pesticide residues was determined to be between 50 and 100 ppm.

The hemp sample was dried and pulverized to less than 0.1 mm by a grinder. The water content of the pulverized *cannabis* sample was less than 3%. 1,000 kg of the pulverized *cannabis* sample were loaded into a solvent extraction apparatus, and extracted with 25,000 L ethanol.

The ethanol-*cannabis* extract was diluted with water so that 40% of the final volume was water. The diluted extract was filtered to remove any insoluble matter, and the supernatant was pumped into a stainless steel chromatographic column with a height to diameter ratio of 5:1 and a volume of 500 L. The chromatographic column was packed with the polymer made in Example 1.

The mobile phase used was 60% ethanol solution in an isocratic mode. The flow rate was about 1000 L/hr to about 1500 L/hr and the column temperature was kept at room temperature.

Fractions flowing out from the chromatographic column were collected, wherein the volume each fraction was the same of the column volume.

Fractions were analyzed for the presence of cannabinoids and pesticide active ingredients at a detection wavelength of 220 nm. The first two fractions contained pesticide active ingredients. The $3^{rd}$ and $4^{th}$ fractions contained CBD. The $5^{th}$ to the $6^{th}$ fractions contained a mixture of CBG, CBV, and CBN.

The $3^{rd}$ and $4^{th}$ fractions were combined and ethanol was removed using a membrane machine and a single effect concentrator. A concentrated solution was obtained by removing 90% or more of methanol. The concentrated solution contained CBD.

The $5^{th}$ to the $6^{th}$ fractions were combined and ethanol was removed using a membrane machine and a single effect concentrator. A concentrated solution was obtained by removing 90% or more of ethanol. The concentrated solution contained CBG, CBV, and CBN.

To isolate and purify CBD, the concentrated solution was mixed with a heptane solvent. The temperature of the mixture was lowered to about −5° C. so that CBD could be crystalized. The crystallization temperature was −5° C. and the crystallization time was 5 hours.

Once the crystallization step was complete, the CBD crystal was filtered and dried in a double cone vacuum dryer, where the drying temperature was 60° C. and duration was for 6 hours. During the drying process, the solvent was removed obtain a CBD product with a purity of 99% or higher.

The $1^{st}$ and $2^{nd}$ fractions were combined and ethanol was removed using a membrane machine and a single effect concentrator. A concentrated solution was obtained by removing 90% or more of ethanol. The concentrated solution contained the removed pesticide active ingredients. This concentrated solution was mixed with hydrogen peroxide. For each kg of the concentrated solution, 0.05 kg of hydrogen peroxide was added. The mixture was then heated to 80° C. for 2 hours to denature the removed pesticide active ingredients.

Example 11—Pesticide Active Ingredient Removal

A *cannabis* sample, namely flowers, leaves, and stem of an industrial hemp plant, was obtained.

The quantity of pesticide active ingredients in the *cannabis* sample was determined using Agilent Gas Chromatograph 6890N. The used parameters were: (i) column: 30 m×0.32 mm capillary column Bonded DB-5 (5% benzyl silicone), film thickness 0.25 um; (ii) temperature: oven temperature: 240° C.; (iii) inlet temperature (gasification chamber) 260° C.; (iv) detection chamber 280° C.; (v) gas flow rate: carrier gas (nitrogen) 2.0 ml/min; (vi) air 300 ml/min; (vii) hydrogen 30 ml/min; (x) Split ratio: 20:1; and (xi) injection volume: 1.0 μl. The content of pesticide residues was determined to be between 50 and 100 ppm.

The *cannabis* sample was pulverized to less than 0.1 mm by a grinder. The water content of the pulverized *cannabis* sample was less than 3%. 500 kg of the pulverized *cannabis* sample were loaded into a solvent extraction apparatus, and extracted with 12,500 L heptane.

The heptane-*cannabis* extract was concentrated by removing heptane using a concentrator.

The concentrated extract was mixed with ethanol so that 60% of the final volume was ethanol. The diluted extract was filtered to remove any insoluble matter, and the supernatant was pumped into a stainless steel chromatographic column with a height to diameter ratio of 5:1 and a volume of 500 L. The chromatographic column was packed with the polymer made in Example 1.

The mobile phase used was 60% ethanol solution in an isocratic mode. The flow rate was about 1000 L/hr to about 1500 L/hr and the column temperature was kept at room temperature.

Fractions flowing out from the chromatographic column were collected, wherein the volume each fraction was the same of the column volume.

Fractions were analyzed for the presence of cannabinoids and pesticide active ingredients at a detection wavelength of 220 nm. The first two fractions contained pesticide active ingredients. The $3^{rd}$ and $4^{th}$ fractions contained CBD. The $5^{th}$ to the $6^{th}$ fractions contained a mixture of CBG, CBV, and CBN.

The $3^{rd}$ and $4^{th}$ fractions were combined and ethanol was removed using a membrane machine and a single effect concentrator. A concentrated solution was obtained by removing 90% or more of methanol. The concentrated solution contained CBD.

The $5^{th}$ to the $6^{th}$ fractions were combined and ethanol was removed using a membrane machine and a single effect concentrator. A concentrated solution was obtained by removing 90% or more of ethanol. The concentrated solution contained CBG, CBV, and CBN.

To isolate and purify CBD, the concentrated solution was mixed with a heptane solvent. The temperature of the mixture was lowered to about −5° C. so that CBD could be crystalized. The crystallization temperature was −5° C. and the crystallization time was 5 hours.

Once the crystallization step was complete, the CBD crystal was filtered and dried in a double cone vacuum dryer, where the drying temperature was 60° C. and duration was for 6 hours. During the drying process, the solvent was removed obtain a CBD product with a purity of 99% or higher.

The $1^{st}$ and $2^{nd}$ fractions were combined and ethanol was removed using a membrane machine and a single effect concentrator. A concentrated solution was obtained by removing 90% or more of ethanol. The concentrated solution contained the removed pesticide active ingredients. This concentrated solution was mixed with hydrogen peroxide. For each kg of the concentrated solution, 0.05 kg of hydrogen peroxide was added. The mixture was then heated to 80° C. for 2 hours to denature the removed pesticide active ingredients.

Example 12—Pesticide Residues in Industrial Hemp Samples Used in Example 11

The industrial hemp sample used in Example 11 was tested to determine the presence of any one of the five commonly-used pesticides to cultivate industrial hemp. The five commonly-used pesticides are α-naphthaleneacetic acid, clethodim, octanoyl bromoxynil, chlorpyrifos, and cyhalothrin.

The table below summarizes the respective concentrations of -naphthaleneacetic acid, clethodim, octanoyl bromoxynil, chlorpyrifos, and cyhalothrin in the industrial hemp sample.

| Pesticide | Concentration (ppm) | Reference Standard | Detection Method |
|---|---|---|---|
| α-naphthaleneacetic acid | ≤10 | GB22614 | Gas chromatography |
| clethodim | ≤50 | SN0346 | High performance liquid chromatography (HPLC) |
| octanoyl bromoxynil | ≤25 | HGT4466 | Gas chromatography |
| chlorpyrifos | ≤10 | GB19604 | HPLC |
| cyhalothrin | ≤50 | GB20695 | HPLC |

To determine the concentration of α-naphthaleneacetic acid in the hemp sample, the following protocols were followed:

Reagents: diethyl ether, petroleum ether (distillation range 30-60° C.), diethyl ether-petroleum ether (4:1), anhydrous sodium sulfate (burned at 650° C. for 4 hours, and after cooling, stored in a closed container); hydrochloric acid solution: 1 mol/L, and α-naphthaleneacetic acid standard product: purity 99%.

To prepare α-naphthalene acetic acid standard solution: weigh an appropriate amount of α-naphthalene acetic acid standard product, and use diethyl ether-petroleum ether (4:1) to prepare a standard stock solution with a concentration of 0.10 mg/mL.

To prepare a sample solution: weigh 15 g of sample and place the sample into a 50 mL centrifuge tube; add 2 mL of hydrochloric acid solution (1 mol/L) and mix well; add 0.5 g of anhydrous sodium sulfate; add 10 mL of ether-petroleum ether (4:1); mix on a vortex mixer for 1 min; centrifuge at 3000 r/min for 2 min; transfer the ether layer to a KD concentrating bottle. The residue was extracted once with 5 mL of ether-petroleum ether (4:1). Combine the organic phases and place them on a multifunctional micro sample processor, ventilate at 40° C., and concentrate to a constant volume of 0.20 mL for gas chromatography determination.

Chromatographic conditions:
  Capillary column: HP-1 (dimethvlpolysiloxane Gum) 10 m×0.53 mm (inner diameter)×2.65 um fused silica or equivalent capillary column;
  Column temperature: 165° C.
  Inlet temperature: 230° C.
  Detector temperature: 250° C.;

Carrier gas, makeup gas: nitrogen (purity 99.99%), column flow rate 8 mL/min, makeup gas flow rate 30 mL/min;
Hydrogen: 40 ml/min; and
Air: 400 mL/min.
Concentration calculation:

$$X = \frac{h \times c \times V}{h_s \times m}$$

X: the residual amount of α-naphthalene acetic acid in the sample, mg/kg;
h: the peak height of α-naphthalene acetic acid in the sample solution, mm;
$h_s$: the peak height of α-naphthalene acetic acid in the standard working solution, mm;
c: the concentration of α-naphthalene acetic acid in the standard working solution, ug/mL;
V: The final constant volume of the sample solution, mL; and
m: the amount of sample weighed, g.
The blank value was deducted from the calculation result.

To determine the concentration of clethodim in the hemp sample, the following protocols were followed:
Reagents: acetonitrile, freshly distilled water, acetone, petroleum ether, phosphoric acid, acetone petroleum ether solution: (acetone: petroleum ether; 1:1), clethodim lithium salt standard sample: the known mass fraction of clethodim lithium salt, M≥98.0%.
To prepare a clethodim standard solution: weigh 0.1 g of clethodim lithium salt standard sample; place the clethodim lithium salt in a 50 mL volumetric flask; add 3 drops of glacial acetic acid and a small amount of acetone petroleum ether solution to shake to dissolve; dilute with acetone petroleum ether and shake well. Use a pipette to transfer 5 mL of the diluted solution into a 50 mL volumetric flask, dilute with petroleum ether and acetone solution, and shake well.
To prepare a sample solution: weigh a sample containing 0.1 g of clethodim; place the clethodim in a 50 mL volumetric flask; dilute to the mark with acetone petroleum ether solution; and shake it well. Use a pipette to transfer 5 mL of the solution into a 50 mL volumetric flask, dilute to the mark with petroleum ether and acetone solution, and shake well.
Chromatographic conditions:
Mobile phase: acetonitrile:water=65:35, where pH was adjusted to 3.0 with phosphoric acid, filtered through a membrane, and degassed;
Flow rate: 1.0 mL/min;
Column temperature: room temperature (the temperature difference should not be greater than 2° C.)
Detection wavelength: 254 nm;
Injection volume: 10 vl;
Retention time: about 5-8 min.
Concentration calculation:

$$w_1 = \frac{A_2 \times m_1 \times w}{A_1 \times m_2} \times \frac{359.90}{365.84}$$

$A_1$: the average value of clethodim peak area in the standard solution;
$A_2$: the average value of clethodim peak area in the sample solution;
$m_1$: the mass (g) of the standard sample;
$m_2$: the mass (g) of the sample;
w: the mass fraction of clethodim lithium salt in the standard sample, expressed in %;
359.90: the relative molecular mass of clethodim; and
365.84: the relative molecular mass of clethodim lithium salt.

To determine the concentration of octanoyl bromoxynil in the hemp sample, the following protocols were followed:
Reagents: chloroform, standard bromoxynil octanoyl sample (known mass fraction of bromoxyn octanoyl nitrile, W>98.5%), dicyclohexyl phthalate, and dicyclohexyl phthalate.
To prepare an octanoyl bromoxynil standard solution: weigh 0.05 g of the standard sample of bromoxynil octanoyl and place it in a 15 mL glass bottle with a stopper. Use a pipette to add 5 mL of the internal standard solution and shake well.
To prepare a sample solution: weigh a sample containing 0.05 g of bromoxynil octanoyl (accurate to 0.0001 g) and place it in a 15 mL glass bottle with a stopper. Use the same pipette used in 3.5.1 to add 5 mL of the internal standard solution, shake uniform.
Chromatographic conditions:
chromatographic column: 30 mXO.32 mm capillary column, bonded with DB-5 (5% benzyl silicone), film thickness 0.25 um;
hydrogen flame ionization detector;
column temperature: 240° C.;
vaporization chamber temperature: 260° C.;
detection chamber temperature: 280° C.;
gas flow (mL/min): carrier gas (N2) 2.0, hydrogen 30, air 300;
split ratio: 20:1; and
injection volume 1.0 VL.
Concentration calculation:

$$w_1 = \frac{r_2 m_1 w}{r_1 m_2}$$

$w_1$: the mass fraction of bromoxynil octanoyl in the sample, expressed in %;
$r_2$: the average value of the ratio of the peak area of bromoxynil octanoyl and the peak area of the internal standard substance in the sample solution;
$m_1$: the mass (g) of the standard sample;
w: the mass fraction of bromoxynil octanoyl in the standard sample, expressed in %;
$r_1$: the average value of the ratio of the peak area of bromoxynil octanoyl and the peak area of the internal standard substance in the standard solution;
$m_2$: The mass (g) of the sample.

To determine the concentration of chlorpyrifos in the hemp sample, the following protocols were followed:
Reagents: acetonitrile, acetic acid, double-distilled water, chlorpyrifos standard sample: the known mass fraction of chlorpyrifos 99.0%.
To prepare a standard chlorpyrifos solution: weigh 0.1 g of chlorpyrifos standard sample, place it in a 100 mL volumetric flask, dissolve and dilute to the mark with mobile phase, and shake well.
To prepare a sample solution: weigh a sample containing 0.1 g of chlorpyrifos (accurate to 0.0002 g), place it in a 100 mL volumetric flask, dissolve and dilute to the mark with mobile phase, and shake it well.

Chromatographic conditions:
Column: 200 mm×4.6 mm, C18, 5 um
Acetonitrile:water:acetic acid=82:17.5:0.5
Flow rate: 1.0 mL/min;
Detection wavelength: 290 nm;
Injection volume: 5 vL
Column temperature: room temperature Concentration calculation:

$$w_1 = \frac{A_2 \times m_1 \times w}{A_1 \times m_2}$$

$A_1$: the average peak area of chlorpyrifos in the standard solution;
$A_2$: The average value of the peak area of chlorpyrifos in the sample solution;
$m_1$: the mass (g) of the standard sample;
$m_2$: The mass (g) of the sample;
w: the mass fraction of chlorpyrifos in the standard sample.

To determine the concentration of cyhalothrin in the hemp sample, the following protocols were followed:

Reagents: n-hexane, tetrahydrofuran, and lambda-cyhalothrin (known mass fraction ≥98.0%).

To prepare a cyhalothrin standard solution: weigh 0.05 g of lambda-cyhalothrin standard sample (accurate to 0.0002 g), place it in a 50 mL volumetric flask, add 40 mL of mobile phase, and place it in an ultrasonic bath for ultrasonic dissolution for 10 min. Take it out, cool to room temperature, make the volume constant with mobile phase, and shake well.

To prepare a sample solution: weigh 0.05 g of the sample (accurate to 0.0002 g), place it in a 50 mL volumetric flask, add 40 mL of mobile phase, and place it in an ultrasonic bath for ultrasonic dissolution for 10 minutes. Take it out, cool to room temperature, make the volume with mobile phase, shake well.

Chromatographic conditions:
Chromatographic column: 4.6 mm×250 mm, packed with ZORBAX RX-SIL, 5 um particle size packing
Mobile phase: volume ratio (n-hexane:tetrahydrofuran) =99.3:0.7
Mobile phase flow: 2.0 mL/min;
Detection wavelength: 278 nm
Column temperature: room temperature
Injection volume: 10 vl Concentration calculation:

$$w_1 = \frac{A_2 \times m_1 \times w}{A_1 \times m_2}$$

$A_1$: the average value of the peak area of lambda-cyhalothrin in the standard solution;
$A_2$: the average value of the peak area of lambda-cyhalothrin in the sample solution;
$m_1$: the mass (g) of the standard sample;
$m_2$: the mass (g) of the sample;
w: the mass fraction of lambda-cyhalothrin in the standard sample, %.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A method for making a polymer for use in liquid chromatography or solid phase extraction, the method comprising:
polymerizing styrene and divinylbenzene to form a styrene-divinylbenzene copolymer;
soaking the styrene-divinylbenzene copolymer in a swelling agent to form nano-scale micropores; and
soaking the microporous styrene-divinylbenzene copolymer in methanol.

2. The method according to claim 1, wherein polymerizing styrene and divinylbenzene comprises:
adding the styrene, the divinylbenzene, a polymerization initiator, and a pore-forming agent to an organic medium to form a mixture; and
heating the mixture to initiate a polymerization reaction and to form, by the polymerization reaction, the styrene-divinylbenzene copolymer.

3. The method according to claim 1, wherein the molar ratio of the styrene to the divinylbenzene is in a range of 0.8:1 to 1.2:1.

4. The method according to claim 2, wherein the polymerization initiator comprises one or more of azobisisobutyronitrile and benzoyl peroxide.

5. The method according to claim 2, wherein a number of moles of the polymerization initiator used is 1 to 2% of a number of moles of the styrene.

6. The method according to claim 2, wherein the pore-forming agent comprises polyethylene glycol.

7. The method according to claim 2, wherein the organic medium comprises a mixture of polyethylene glycol and liquid paraffin.

8. The method according to claim 7, wherein the volume ratio of polyethylene glycol and liquid paraffin is in a range of 0.8:1 to 1.2:1.

9. The method according to claim 1, wherein the swelling agent comprises one or more of chloroform, methanol or ethanol.

10. The method according to claim 1, wherein a number of moles of the swelling agent used is 30 to 40% of a number of moles of the styrene.

11. The method according to claim 1, wherein the styrene-divinylbenzene copolymer is soaked in the swelling agent at a temperature between 30° C. and 40° C.

12. The method according to claim 1, wherein the styrene-divinylbenzene copolymer is soaked in the swelling agent for 3 to 4 hours.

13. The method according to claim 1, wherein the nano-scale micropores have a pore diameter of 0.4 to 0.6 nm.

14. The method according to claim 1, wherein soaking the microporous styrene-divinylbenzene copolymer in methanol comprises modifying the surfaces of the nano-scale micropores and thereby permitting diffusion of an analyte into and out of the micropores to achieve separation and recovery of the analyte when the polymer is used in liquid chromatography or solid phase extraction.

15. The method according to claim 14, wherein soaking the microporous styrene-divinylbenzene copolymer in methanol comprises smoothing the surfaces of the nano-scale micropores.

16. The method according to claim 1, wherein the microporous styrene-divinylbenzene copolymer has a particle size of 100 to 200 mesh and a pore diameter of 0.4 to 0.6 nm.

17. A polymer for liquid chromatography or solid phase extraction, the polymer being made in accordance with the method of claim 1.

18. A method for preparing a *cannabis* extract, the method comprising:
- preparing a chromatographic column packed with the polymer made in accordance with claim 1;
- obtaining *cannabis* plant material;
- treating the *cannabis* plant material with a solvent to thereby produce a *cannabis* extract;
- passing the *cannabis* extract through the chromatographic column arranged to fractionate at least one cannabinoid out from the *cannabis* extract; and
- collecting the fraction containing the cannabinoid to thereby obtain a pure cannabinoid preparation.

19. The method according to claim 18, the method further comprising:
- passing the *cannabis* extract through the chromatographic column arranged to fractionate pesticide active ingredients out from the *cannabis* extract; and
- collecting the fraction containing the pesticide active ingredients.

20. The method according to claim 18, wherein:
the *cannabis* plant material comprises industrial hemp; and
the pure cannabinoid preparation comprises (—)-trans-$\Delta$-9tetrahydrocannabinol (THC) or cannabodiol (CBD).

* * * * *